United States Patent [19]

Mobley et al.

[11] 4,043,346
[45] Aug. 23, 1977

[54] CATHETER

[75] Inventors: David F. Mobley; Neil H. Baum, both of Houston, Tex.

[73] Assignee: Baylor College of Medicine, Houston, Tex.

[21] Appl. No.: 665,647

[22] Filed: Mar. 10, 1976

[51] Int. Cl.² .................................. A61M 25/00
[52] U.S. Cl. ........................ 128/349 R; 128/244; 128/343
[58] Field of Search ........................ 128/348-351, 128/343, 345, 243, 244, 347

[56] References Cited

U.S. PATENT DOCUMENTS

| 2,616,429 | 11/1952 | Merenlender | 128/350 R |
| 3,108,595 | 10/1963 | Overment | 128/350 R |
| 3,592,197 | 7/1971 | Cohen | 128/349 R |
| 3,807,408 | 4/1974 | Summers | 128/349 R |
| 3,815,608 | 6/1974 | Spinosa et al. | 128/349 R |

Primary Examiner—Dalton L. Truluck
Attorney, Agent, or Firm—Fulbright & Jaworski

[57] ABSTRACT

A catheter is disclosed which is simple to use, avoids the problems with prior catheters, which is fail-safe and fool-proof and one by which the patient cannot injure himself. The catheter comprises a flexible inner tubular member forming a flow duct, snuggly and slidably disposed in an outer tubular member, and having a rounded expansion tip at its inner end comprised of a plurality of prongs biased outwardly and operable to expand and open on inward movement of the inner tubular member in the outer tubular member to a position where the prongs are beyond the inner end of the outer member and to retract on movement of the inner tubular member outwardly in the outer tubular member to a position where at least a portion of the prongs are within the outer tubular member. The outer end of the inner tubular member extends outwardly sufficiently for this movement and has a circumferentially and outwardly extending shoulder adjacent its outer end to engage and secure an end of a resilient drain tube to the inner tubular member.

Detents, preferably axially spaced, circumferentially extending mating rings and grooves, are disposed on the inner and outer tubular members which releasably lock them in a position where the prongs are expanded and in a position where the prongs are retracted. Drain holes are provided in the outer and inner tubular members and are arranged to register when the inner tubular member is locked in a position where the prongs are expanded. An outwardly facing circumferential shoulder is provided on the expansion tip and intermediate the prongs which limit outward movement of the inner tubular member in the outer tubular member. Preferably, the prongs are formed by longitudinally extending slits in the expansion tip and a portion of the inner tubular member adjacent thereto. Other features and details are disclosed throughout.

14 Claims, 5 Drawing Figures

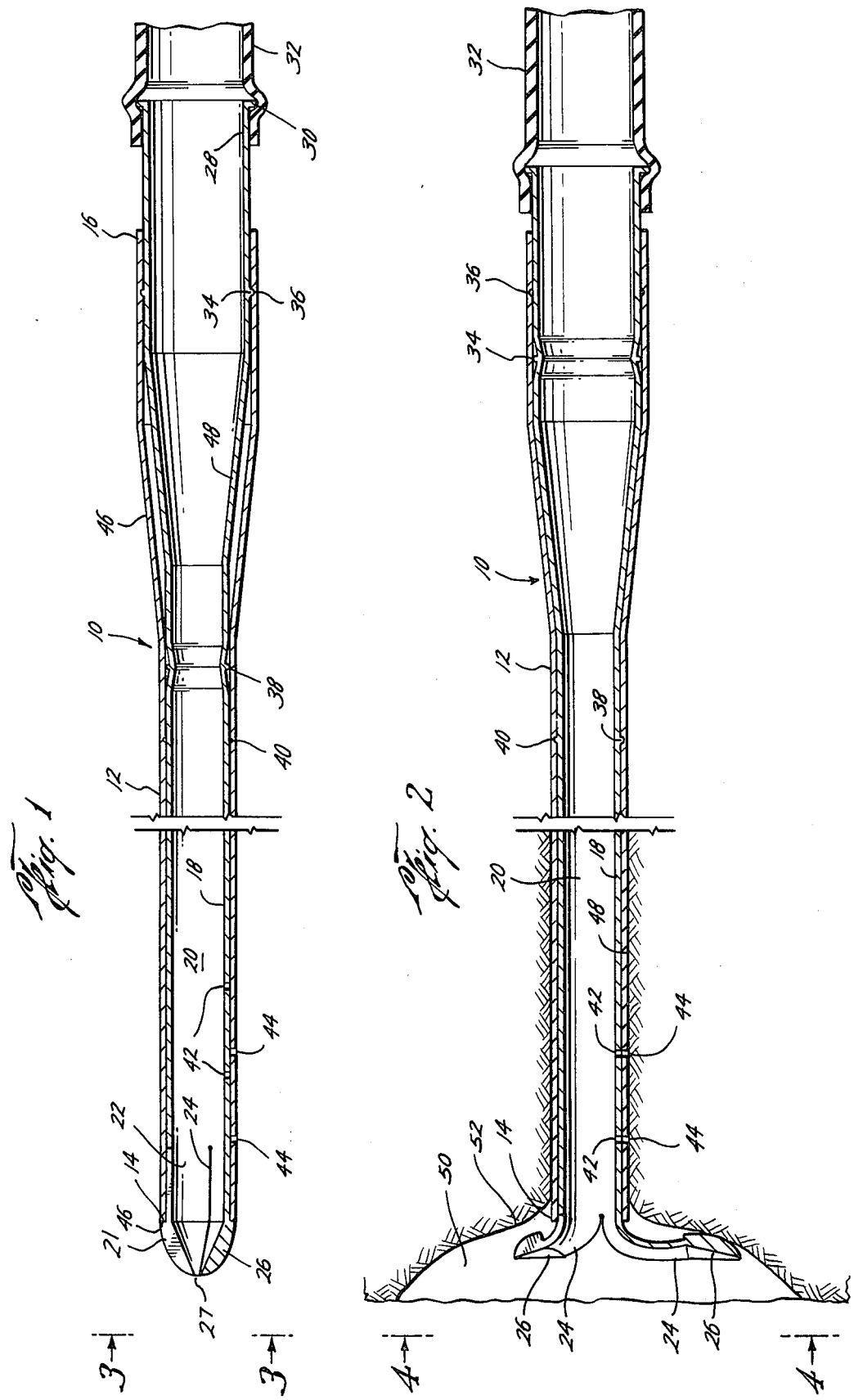

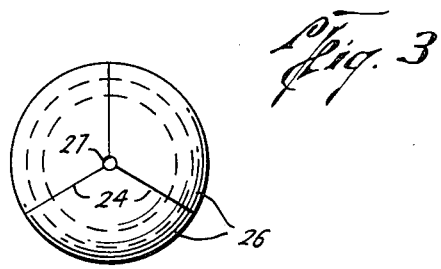
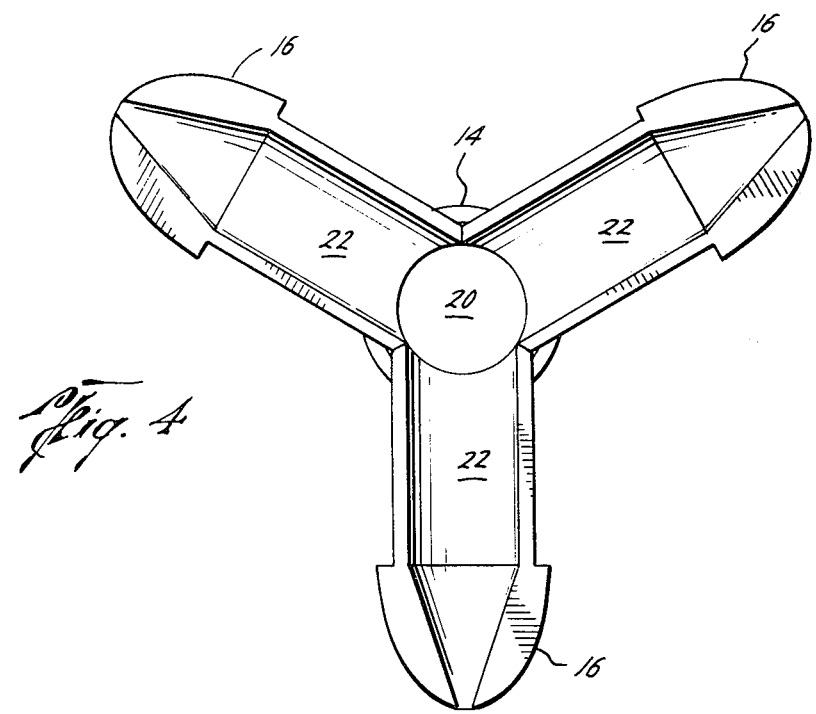
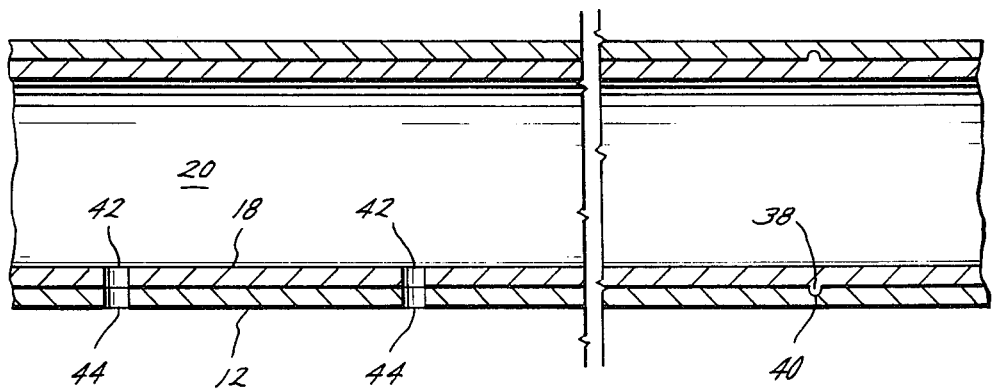

CATHETER

BACKGROUND OF THE INVENTION

The Foley catheter has been the prototype of catheters for some thirty years. It is a balloon catheter and consists of a tube formed of rubber, latex, Silastic, silicone and the like with an inflatable balloon at its inner end which is used to keep the catheter within the bladder. It includes a separate tube to inflate and to deflate the balloon. The only modifications over the years have basically been in the improvement of the rubbers, example, Silastic is superior to latex. The disadvantages of the Foley catheter are: (1) trauma to the urethra, that is, semiconscious or irrational people can pull the inflated balloon through the urethra and the balloon will not deflate. (2) The added expense of the extra lumen for inflating and deflating the balloon. (3) The balloon — may do not work and must be discarded before use and some that work initially later fail. (4) A syringe and sterile water are necessary to fill the balloon which is an extra expense. (5) The balloon can inadvertently be inflated before it reaches the bladder, for example, in the prostatic-urethra. (6) The "puddle phenomonen" — the tip of the Foley catheter rests above the bottom of the bladder and as a result, there always remains excessive urine in the bladder, a constant source of infection. (7) The balloon deflates by itself and the catheter falls out. (8) The balloon cannot be deflated when in place.

The techniques for deflating a Foley balloon that does not deflate are traumatic in itself; for example, (1) a fine wire can be passed through the balloon lumen to puncture it, (2) a large needle can be passed through the abdominal wall to attempt to hit the balloon and puncture it, or (3) the balloon can be inflated with alcohol until it bursts. This irritates the bladder and leaves behind tiny fragments of rubber. If the patient is not taken to the operating room for removal of the rubber fragments, the fragments can serve as a source of bladder stone formation and infection.

For a history of the early development of the balloon catheter, reference is made to Urology, January, 1973, Volume I, No. 1, pages 75 - 80. Also, the following United States patents disclose various proposals for catheters: U.S. Pat. Nos. 88,695; 1,870,924; 1,922,084; 2,050,407; 2,175,726; 2,230,226; 2,259,488; 2,322,858; 2,559,281; 2,259,488; 2,343,579; 2,616,429; 2,642,874; 2,649,092; 2,693,191; 2,849,001; 2,854,983; 2,343,579; 2,915,058; and 3,799,172. None of the catheters disclosed in these patents, however, has been in widespread use, the Foley catheter having been the prototype of indwelling urethral catheters for the last 30 years, as previously mentioned.

It would be highly advantageous to provide a catheter in which there is no extra lumen to decrease urine drainage surface area, in which there is no balloon to cause the above mentioned problems with balloons, where no syringe is required, which is simpler to use than the Foley catheter, less expensive to manufacture, one in which the patient cannot injure himself, which is virtually fail-safe and fool-proof, in which the puddling phenomona is eliminated, and in which the expansion tip cannot be activated until the catheter is all the way into the bladder.

SUMMARY

The present invention is directed to a catheter which avoids the disadvantages of the Foley or balloon catheter as wellas other prior proposals for catheters, and has the advantages mentioned above.

The disadvantages of the balloon or Foley catheter, as well as the proposals for catheters in the patents set forth above, are eliminated and the foregoing advantages are obtained by a catheter having a flexible inner tubular member forming a flow duct snuggly and slidably disposed within a flexible outer tubular member. The inner tubular member has a rounded expansion tip at its inner end and is open at its outer end. The expansion tip is comprised of a plurality of prongs biased outwardly and operable to expand and open on inward movement of the inner tubular member in the outer tubular member to a position where the prongs are beyond the inner end of the outer tubular member and to retract on movement of the inner tubular member outwardly in the outer tubular member to a position where at least a portion of the prongs are within the outer tubular member.

Preferably, the rounded expansion tip projects beyond the inner end of the outer tubular member in retracted position and it and a portion of the inner tubular member adjacent thereto are slotted longitudinally to form the prongs. An opening is provided in the tip so that when the catheter gets to the bladder, urine starts to flow through it, giving an indication that the tip is in the bladder.

Releasable detents, preferably circumferentially extending rings and grooves, are provided on the tubular members which releasably lock them in a position where the prongs are expanded and in a position where the prongs are retracted. Also, drain holes are provided in these tubular members which register when the prongs are in expanded position. Other features and details appear throughout.

Accordingly, it is an object of the present invention to provide an improved catheter which avoids the disadvantages of the so-called Foley or balloon catheter.

It is a further object to provide a catheter in which there is no extra lumen to decrease urine drainage surface area.

It is a further object of the present invention to provide an improved catheter which is simple to use, less expensive to manufacture, and one which is virtually fail-safe and fool-proof and one by which the patient cannot injure himself and the puddling phenomonon is eliminated.

Still a further object of the present invention is to provide such a catheter in which no syringe is required and there is no balloon to cause the above mentioned problems with balloons. A further object of the present invention is the provision of such a catheter which is relatively inexpensive and simple to use.

Other and further objects, features and advantages of the invention will appear throughout.

BRIEF DESCRIPTION OF THE DRAWINGS

FIG. 1 is a side view, in section, of an improved catheter according to the invention and shown with its expansion tip in retracted position.

FIG. 2 is a view similar to that of FIG. 1 but illustrates the improved catheter within the urethra and the expansion tip prongs expanded against the lower wall of the bladder.

FIG. 3 is a view taken along the line 3—3 of FIG. 1.

FIG. 4 is a view taken along the line 4—4 of FIG. 2.

FIG. 5 is an enlarged, fragmentary view, in section better illustrating the releasable detents locking the inner and outer tubular members in a position where the expansion tip is expanded, and the drain holes in these members are in registry thus permitting drainage from the urethra into the flow duct in the inner tubular member.

DESCRIPTION OF THE PREFERRED EMBODIMENTS

Referring to the drawings and particularly to FIGS. 1 and 2, the improved catheter is generally designated by the reference numeral 10 and includes a flexible outer tubular member 12 which is open at its inner end 14 and its outer end 16. A flexible inner tubular member 18 forming the flow duct 20 is snuggly and slidably disposed within the outer tubular member 12.

The inner end of the inner tubular member 18 has a rounded expansion tip 21 which is slotted along with the inner portion 22 at the inner end of the inner tubular member by the longitudinally extending slots 24 to form the expansion prongs 26 which are biased outwardly but are maintained in retracted position when the inner and outer tubular members 20 and 12, respectively, are in the position illustrated in FIG. 1. While any number of slots 24 may be provided, satisfactory results are obtained by using three such slots to form three prongs as illustrated in FIGS. 3 and 4. A small opening 27, for example about 2 mm., is provided in the tip 21 so that body fluid, for example urine, starts to flow through the catheter 10 when the tip 21 enters the bladder 50 thereby indicating that the tip 21 is in the bladder 50.

Referring again to FIG. 1, the outer end 28 of the inner tubular member 10 is provided with an outwardly extending circumferential shoulder 30 which provides a means for securing a flexible, resilient drain tube 32 to provide a continuation of the flow duct 20 for disposal of urine or other body fluids and the like.

In order to releasably fix or lock the catheter so that the inner and outer tubular members are in a position where the expansible tip 16 is in retracted position and the expansible tip is in expanded position, the detents 40 are provided on the inner 18 and outer tubular members 12, which are here illustrated as the circumferential extending, mating shoulders and grooves 34 and 36 and 38 and 40.

The drain holes 42 and 44 are provided in the inner tubular member 18 and outer tubular member 12 but are arranged to be in registery with one another, as illustrated in FIGS. 2 and 5, when the inner tubular member 18 is moved inwardly in the outer tubular member 12 to a position where the expansion tip 16 is in expanded position as best illustrated in FIGS. 2 and 5.

Preferably, the outer and inner tubular members 12 and 18 are tapered outwardly at 46 and 48, respectively, to provide an enlarged flow duct for drainage of urine and other fluids. This tapered portion is sufficiently far from the expansion tip 21 to be outside the body when in use.

The catheter 12 may be made of any flexible material suitable for insertion into the human body, and in which the prongs can form a continuation of the inner tubular member and be biased outwardly. A presently preferred material is Silastic which is teflon polymer, although other materials can be used, such as the silicones and the like. Also, the catheter can be made in various sizes, for example, from approximately 8 french diameter to 32/f dia. (1 f. equals 0.33 mm.).

The prongs 24 are molded in their expanded position and hence have "memory" so that when not restrained will expand, yet are readily and easily retractable and will not expand when in the urethra.

In use, the catheter is assembled in the position illustrated in FIG. 1, in which the prongs 26 of the expansion tip 21 are in retracted position by having a portion of them within the inner end 14 of the outer tubular member 12, with the outwardly facing circumferential shoulder of the expansion tip 21 abutting against the inner end 14 of the outer tubular member thereby limiting inward movement of the inner tubular member 18 and the outer tubular member 12. The catheter 10 is releasably locked in this position by the engagement of the detents 34 and 36, and in this position, is inserted into the urethra 48 until the expansion tip 21 enters the bladder 50, which is indicated by urine entering the opening 27 and starting to flow through the catheter 10. The inner tubular member 18 is then moved inwardly in the outer tubular member 12 until the prongs 26 project beyond the end 14 of the outer tubular 12 thus permitting them to expand and engage the lower wall 52 of the bladder 50. The detents 38 and 40 engage and releasably lock the inner and outer tubular members 18 and 12 in this position. In addition, the drain holes 42 and 44 are in registery with one another permitting fluids in the urethra to drain into the flow duct 20 in the interior of the inner tubular member 18.

When it is desired to remove the catheter 10, the inner tubular member 18 is moved outwardly in the outer tubular member 12 which causes the slotted portion 22 of the prongs 26 to move outwardly and into the inner end 14 of the outer tubular member 12 thereby retracting them to the position illustrated in FIG. 1, the drain holes 44 and 42 are no longer in registery, the detents 38 and 40 are released and the detents 34 and 36 are reengaged releasably locking the inner and outer tubular members 18 and 12 in the position illustrated in FIG. 1. The catheter 10 may then be withdrawn from the urethra.

It is noted that the expansion tip 21 is expanded and retracted by the simple mechanical movement of sliding the inner tubular member 18 inwardly and outwardly in the outer tubular member 12. This makes the catheter 10 virtually fail-safe and there is no balloon required as well as means to inflate it and deflate it and the like with the balloons' attendant disadvantages and problems.

Also, in the event a patient, who may be delirious, semi-conscious and the like, should grab the catheter 10 and pull it out, no damage would be done to the urethra 48 due to the fact that the expansion tip 21 and the prongs 26 are resiliently biased outwardly and will simply retract upon the movement through the urethra 48. In addition, if the expansion tip is inadvertently moved to a position where it would normally expand while in the urethra, the walls of the urethra would restrain and prevent the opening of the expansion tip until it is in the bladder.

Accordingly, the catheter of the present invention is well suited and adapted to attain the objects and ends and has the advantages and features mentioned and others inherent therein.

While presently preferred embodiments of the invention have been given for the purpose of disclosure, changes may be made therein which are within the spirit of the invention as defined by the appended claims.

What is claimed is:

1. A catheter comprising, a flexible outer tubular member having open inner and outer ends, a flexible inner tubular member forming a flow duct snugly and slidably disposed within the outer tubular member, and the inner tubular member having a rounded expansion tip at its inner end and being open at its outer end, the expansion tip including a drain opening and being comprised of a plurality of prongs biased outwardly and operable to expand and open on inward movement of the inner tubular member in the outer tubular member to a position where the prongs are beyond the inner end of the outer member and to retract on movement of the inner tubular member outwardly in the outer tubular member to a position where at least a portion of the prongs are within the outer tubular member, the outer end of the inner tubular member being extendable outwardly and inwardly of the outer end of the outer tubular member a distance sufficient for the movement of the inner tubular, member to expand and to retract the prongs.

2. The catheter of claim 1, including releasable detents on the inner and the outer tubular members releasably locking them in a position where the prongs are expanded and in a position where the prongs are retracted.

3. The catheter of claim 1 including, a circumferentially and outwardly extending shoulder adjacent the outer end of the inner tubular member arranged to engage and secure an end of a resilient drain tube, and a circumferentially extending and outwardly facing shoulder intermediate the ends of the prongs engaging the inner end of the outer tubular member when the prongs are in the retracted position thereby limiting outward movement of the inner tubular member in the outer tubular member.

4. The catheter of claim 1 including, releasable detents on the inner and outer tubular members releasably locking the inner tubular member in a position in the outer tubular member where the prongs are expanded and in a position where the prongs re retracted.

5. The catheter of claim 4 where the releasable detents comprise axially spaced circumferentially extanding mating rings and grooves on the tubular members.

6. The catheter of claim 1 where, the inner and outer tubular members have drain holes arranged to register when the inner tubular member is in a position in the outer tubular member where the prongs are expanded, thereby permitting drainage into the inner tube, the drain holes being adjacent the expansion tip.

7. The catheter of claim 1 where, the rounded expansion tip projects beyond the inner end of the outer tubular member, the expansion tip and a portion of the inner tubular member at its inner end and adjacent the expansion tip being slotted longitudinally to form the prongs, the prongs expanding when the expansion tip and the slotted portion is moved inwardly beyond the inner end of the outer tubular member and retracting when the slotted portion is moved outwardly and into the inner end of the outer tubular member.

8. The catheter of claim 1 where, the inner and outer tubular members are tapered outwardly adjacent their outer ends, and the inner tubular member includes a circumferentially and outwardly extending shoulder adjacent its outer end arranged to engage and secure an end of a drain tube.

9. A catheter comprising, a flexible outer tubular member having open inner and outer ends, a flexible inner tubular member forming a flow duct snugly and slidably disposed within the outer tubular member, the inner tubular member having a rounded expansion tip at its inner end comprised of a plurality of prongs biased outwardly and operable to expand and open on movement of the inner tubular member in the outer tubular member to a position where a portion of the prongs are within the outer tubular member, the outer end of the inner tubular member extending outwardly of the outer end of the outer tubular member a distance sufficient for the movement of the inner tubular member to expand and to retract the expansion tip, the expansion tip including a restricted drain opening when retracted and providing an unrestricted drain opening when expanded, a circumferentially extending shoulder on the outer end of the outer tubular member and providing means for securing an end of a drain tube to the inner tubular member, a circumferential and outwardly facing shoulder on the expansion tip engageable with the inner end of the outer tubular member thereby limiting outward movement of the inner tubular member in the outer tubular member, and releasable detents on the inner and the outer tubular members releasably locking them in a position where the prongs are expanded and in a position where the prongs are retracted.

10. The catheter of claim 9 where, the releasable detents comprise axially spaced circumferentially extending mating rings and grooves on the tubular members.

11. The catheter of claim 9 where, the inner and outer tubular members have drain holes adjacent the prongs arranged to register when the inner tubular member is in a position where the prongs are expanded.

12. The catheter of claim 9 where, the releasable detents comprise axially spaced circumferentially extending mating rings and grooves on the inner and outer tubular members, and the inner and outer tubular members have drain holes adjacent the prongs arranged to register when the inner tubular member is in a position where the prongs are expanded.

13. The catheter of claim 9 where, the rounded expansion tip projects beyond the inner end of the outer tubular member, the expansion tip and a portion of the inner member at its inner end and adjacent the expansion tip being slotted longitudinally to form the prongs, the prongs expanding when the expansion tip and the slotted portion is moved inwardly beyond the inner end of the outer tubular member and to retract when the slotted portion is moved outwardly and into the inner end of the outer tubular member.

14. The catheter of claim 9 where, the rounded expansion tip has an opening for flow of body fluid.

* * * * *